(12) United States Patent
Overmyer

(10) Patent No.: US 6,250,920 B1
(45) Date of Patent: Jun. 26, 2001

(54) PURGE SYSTEM FOR FLUSHING AND DISINFECTING DENTAL UNITS

(76) Inventor: Thad J. Overmyer, 337 E. Lexington Ave., Danville, KY (US) 40422

( * ) Notice: Subject to any disclaimer, the term of this patent is extended or adjusted under 35 U.S.C. 154(b) by 0 days.

(21) Appl. No.: 09/465,325

(22) Filed: Dec. 17, 1999

(51) Int. Cl.7 .................................................. A61G 17/02
(52) U.S. Cl. ................................................. 433/80; 433/82
(58) Field of Search .................................. 433/80, 82, 84, 433/98, 104, 106

(56) References Cited

U.S. PATENT DOCUMENTS

| | | | |
|---|---|---|---|
| 3,718,973 | * | 3/1973 | Slater et al. . |
| 4,668,190 | * | 5/1987 | Overmyer .............................. 433/80 |
| 5,295,829 | * | 3/1994 | Frey et al. .............................. 433/82 |
| 5,308,579 | * | 5/1994 | Melon .................................... 422/28 |
| 5,318,443 | * | 6/1994 | Overmyer ............................. 433/104 |
| 5,360,338 | * | 11/1994 | Waggoner ............................... 433/80 |
| 5,526,841 | * | 6/1996 | Detsch et al. ........................... 137/15 |
| 5,709,546 | * | 1/1998 | Waggoner ............................... 433/82 |
| 5,785,523 | | 7/1998 | Overmyer . |
| 5,837,204 | * | 11/1998 | Prevost et al. ......................... 433/80 |

* cited by examiner

Primary Examiner—Ralph A. Lewis
(74) Attorney, Agent, or Firm—Charles J. Brown, Esq.

(57) ABSTRACT

A selectively operable removable purge unit is provided for flushing and disinfecting a primary line through which water is directed in normal operation of a dental unit to various devices in the unit, the purge unit including a solution reservoir, a double inlet single outlet router valve, an inlet air line removably connectable between a pressurized air source and either the reservoir or the router valve, and lines between the reservoir solution and the router valve and the router valve and the primary water line.

4 Claims, 2 Drawing Sheets

PURGE SYSTEM FOR FLUSHING AND DISINFECTING DENTAL UNITS

BACKGROUND OF THE INVENTION

My U.S. Pat. No. 5,785,523 describes an improved water line flushing and disinfecting system for a dental unit. The principal purpose of that prior art system is to clean all of several water using devices in a dental unit, not only a handpiece but also auxiliary components such as a syringe, scaler, basin and so on. The object is to provide a system integral with a dental unit which can be utilized to eliminate bacteria growth in all water lines of the unit. Periodically, however, it is necessary to purge the dental unit of all disinfectant and water and resume operation with fresh disinfectant and fresh water. The object of the present invention is to provide a detachable purge unit which can be taken from one dental unit to another to carry out periodically the removal of water from the unit, flushing of all water lines with fresh disinfectant, removal of that disinfectant and refilling of the lines of the unit with fresh water.

SUMMARY OF THE INVENTION

In broad form the purge unit of the invention is intended for use with a dental unit including a plurality of devices through which water can be passed from a pressurized water source through a primary water line. Either pressurized air or disinfectant solution from respective sources thereof can be selectively introduced through a double inlet single outlet first router valve into the primary water line. The invention provides a selectively operable removable purge unit for flushing and disinfecting the primary water line and devices. It includes a solution reservoir for containing a disinfectant solution and ullage. A double inlet single outlet second router valve is provided. An inlet air line is removably connectable between the pressurized air source and alternately either the reservoir ullage or a first inlet of the second router valve. Between the reservoir solution and a second inlet of the second router valve is a solution line. A connection line for either air or solutions from the single outlet of the second router valve is removably connected to the primary water line. By this system water can be expelled from the primary water line and devices by pressurized air and replaced with disinfectant solution displaced by pressurized air from the ullage of the reservoir and the solution can then be expelled by pressurized air and replaced with water.

In one form of the invention the pressurized water source is a water bottle connected to the primary water line with the connection line removably connected between the second router valve and the water bottle. In another form of the invention the pressurized water source is a water main connected to the primary water line through the first router valve with the connection line removably connected between the second router valve and the first router valve.

A pressurized regulator may be included in the air inlet line upstream of the reservoir ullage and the first inlet of the second router valve for reducing air inlet line pressure.

That quick disconnect means may be located in the inlet air line for removable connection with the pressurized air source. Second quick disconnect means may be located in the connection line for removable connection with the primary water line.

DESCRIPTION OF PREFERRED EMBODIMENT

Figure 1:
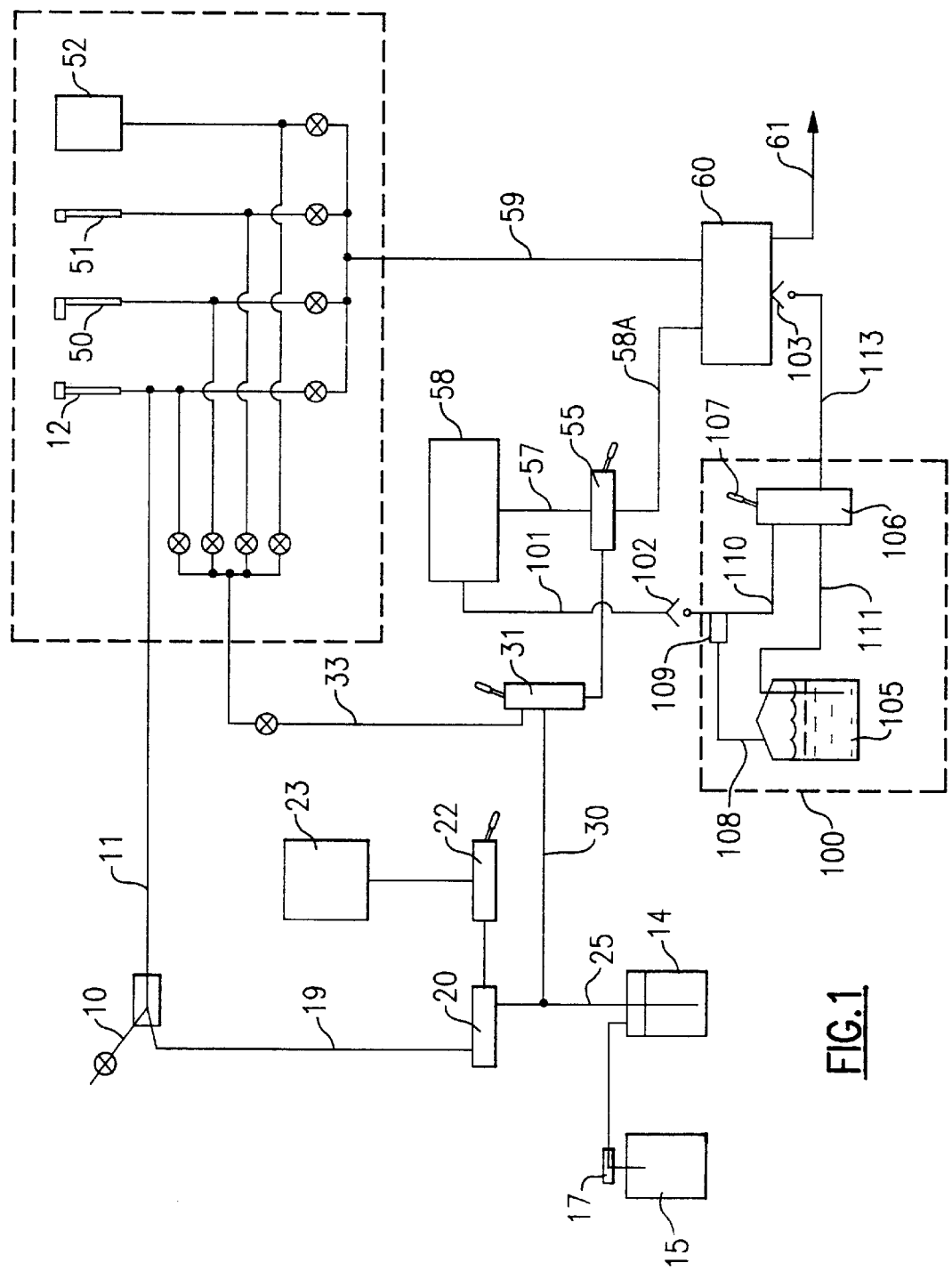
FIG. 1 is a schematic diagram of a known dental water unit with an integral flushing and disinfecting system, but also equipped with the selectively operable removable purge system of the invention, and the pressurized water source is a water bottle.

As noted previously, reference should be had to my U.S. Pat. No. 5,785,523 for a dental unit with a flushing and disinfecting system in which the improvement of the invention has been made. Its full disclosure is incorporated here by reference but it will be described in relation to each of the embodiments of FIGS. 1 and 2 in summary fashion.

Water is delivered through a conduit 10 through a line 11 to a handpiece 12. A reservoir 14 holds a disinfecting and lubricating solution and to the ullage above it air is delivered from a compressed air source 15 through a pressure regulator 17. The water conduit 10 is connected through a line 19 having a single inlet double outlet valve 20 and pneumatic means 22 to a compressed air source 23. A second outlet section 25 of line extends from the valve 20 to the reservoir 14 beneath the level of the solution. Disinfectant solution from the reservoir 14 can be mixed with water from the conduit 10 and delivered through the line 11 to the handpiece 12. Alternatively disinfectant solution alone can be delivered through the line 11 to the handpiece 12.

A branch disinfectant line 30 extends from the line 25 to a single inlet double outlet valve 31, one outlet line 33 of which extends through appropriate valves to various devices in the dental unit such as the handpiece 12, a syringe 50, scaler 51 and basin 52. A double inlet single outlet first router valve 55 has one of its inlets 56 connected to the single outlet of the valve 31 and its other inlet 57 connected to a pressurized air source 58. In the embodiment of both FIG. 1 and FIG. 2 a line 59 extends to the dental unit to carry water, disinfectant solution or air in a manner described below. It connects with the handpiece 12, syringe 50, scaler 51 and basin 52.

All of this constitutes a dental unit which includes a plurality of devices 12, 50, 51 and 52 through which water can be passed from a pressurized water source through the line 59 into which either pressurized air or disinfectant solution from the air source 58 or the solution reservoir 14 can be selectively introduced through the double inlet single outlet first router valve 55. The pressurized water source leading to the line 59 can be either a water reservoir 60 having a valved drain 61 as in the embodiment of FIG. 1. or a water main 76 with a check valve 78 and on-off valve 79 as in the embodiment of FIG. 2.

The apparatus so far described is set forth in my U.S. Pat. No. 5,785,523. The inventive improvement is a selectively operable detachable purge unit for periodically flushing and disinfecting the primary water line 59 and its devices 12, 50, 51 and 52. Essential to the apparatus of the invention is that it is removable, which is to say it can be connected and disconnected to various dental units at will and operated on an as-needed basis. Four steps are carried out by the new purge system. The first is that water is removed from the primary water line 59 and the devices 12, 50, 51 and 52, and this removing of water is accompanied by injection of air through those components and their lines. The next step is that the emptied lines are filled with fresh disinfecting solution which is held there for a recommended time allowing the solution to take effect. The third step is that the disinfectant is then removed from the lines by displacement of air or water. The final step is that new water is replenished in the lines.

Referring now to FIG. 1, the purge unit of the invention is shown encircled by dotted lines 100. The purge unit is removably connectable to a line 101 from the pressurized air source 58 by means of a detachable connection 102. The purge unit is also removably connectable indirectly to a single outlet line 58A of the first router valve 55 by means of a detachable connection 103. Within the purge unit 100 is a reservoir 105 containing a disinfectant solution or water. Also within the purge unit 100 is a double inlet single outlet router valve 106 having a switch 107. The upper ullage within the reservoir 105 is connected by a line 108 through a pressure regulator 109 to a line 110 joining the detachable connection 102 with the router valve 106. Another line 111 joins the liquid disinfectant solution in the reservoir 105 with a second inlet of the router valve 106. An outlet line 113 extends from the router valve 106 to the detachable connection 103.

The operating procedure for the apparatus of FIG. 1 begins with selective attachment of the purge unit 100 by means of the two detachable connections 102 and 103. Any water left in the water bottle 60 is removed through the drain 61. If any small amount of water remains in the bottle 60 it can be blown out by opening any or all of the devices 12, 50, 51 and 52. Router valve 106 is operated to cease entry of air into the line 113 and router valve 31 is operated to cease entry of solution through the router valve 55. Air from the air source 58 passes through the pressure regulator 109 to pressurize the disinfectant solution in the reservoir 105. The router valve 106 is operated so that liquid solution travels from the reservoir 105 through the router valve 106 and thence to the bottle 60. Since the disinfectant enters the lower portion of the bottle 60, which at this point is empty, the disinfectant solution is sprayed against the inside walls of the bottle 60. The devices 12, 50, 51 and 52 are opened to depressurize the system while the disinfectant solution is filling the bottle 60. When the bottle 60 is filled the detachable connections 102 and 103 are removed. The valve 55 is then operated to allow the bottle 60 to be pressurized with air. The devices 12, 50, 51 and 52 are opened so that the disinfectant solution from the bottle 60 passes through the line 59 and out of the devices 12, 50, 51 and 52. The disinfectant solution is held in place for any recommended period of time. Thereafter, the devices 12, 50, 51 and 52 are activated to remove the solution under pressure of air from the bottle 60.

The bottle 60 is then replenished with fresh water by use of a purge system that functions the same as the purge unit described above containing the disinfectant solution. This second purge system contains clean water which is both distilled and potable.

Figure 2:
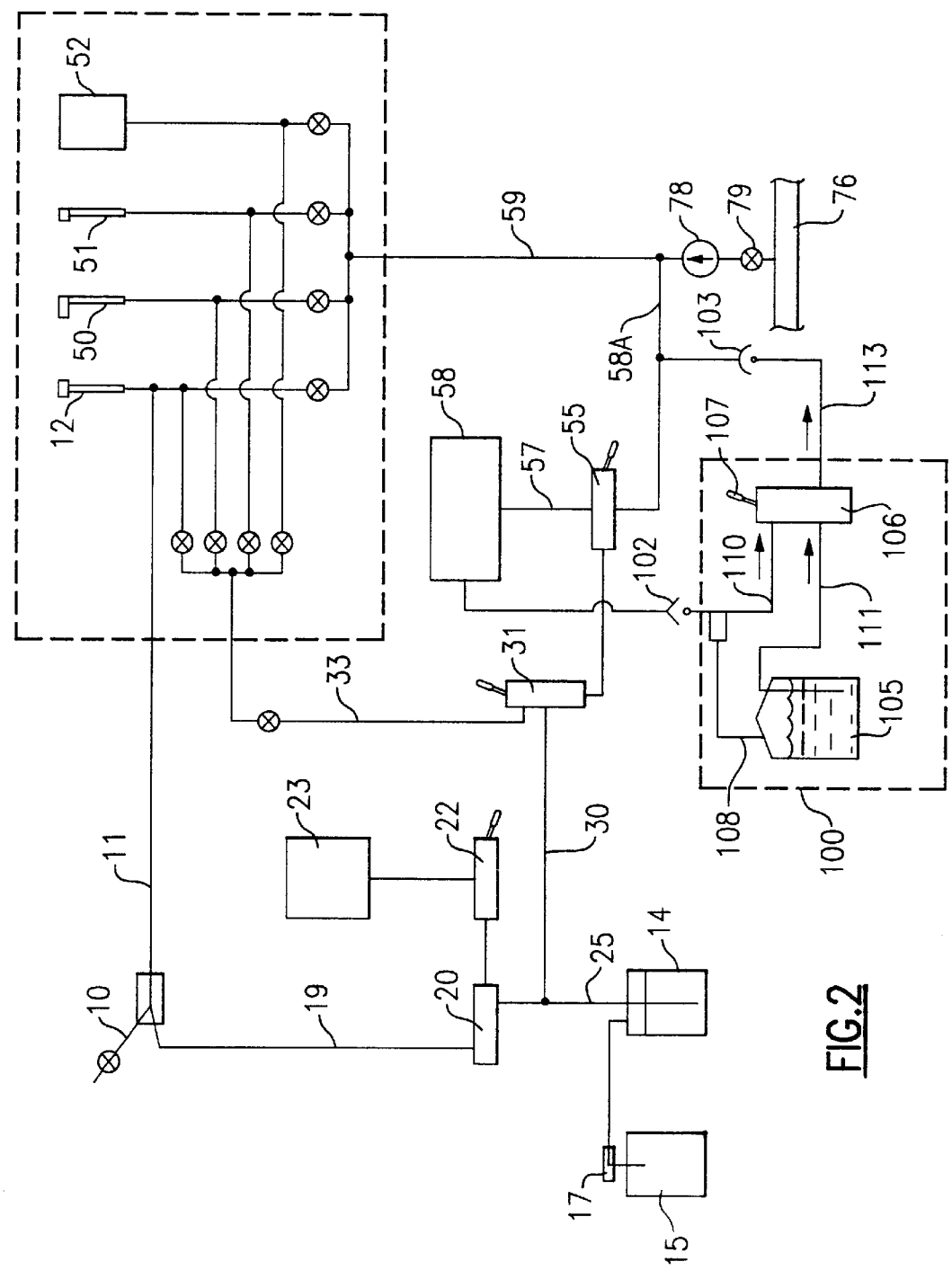
FIG. 2 is a schematic diagram similar to FIG. 1 wherein the pressurized water source is a water main.

The embodiment of FIG. 2 differs from that of FIG. 1 only in that the pressurized water source is the water main 76 rather than the bottle 60. To isolate the dental unit from entry of water from the main 76 the valve 79 is closed. In this embodiment the detachable connection 103 is selectively attachable to the outlet line 58A of the double inlet single outlet valve 55.

When the detachable connections 102 and 103 are attached pressurized air is passed through the line 108 to increase pressure in the reservoir 105. Router valve 106 then directs air into the lines 113 and 59 and up to the devices 12, 50, 51 and 52. These devices are opened to allow air to blow out water. To fill the system with solution the switch 107 is operated so that solution passes from the reservoir 105 through the line 111 to the valve 106 and then through the lines 113, 58A and 59 to the devices 12, 50, 51 and 52. After a suitable hold time the detachable connections 102 and 103 are removed. Water is re-filled throughout by opening the water main valve 79 thereby forcing disinfectant solution out of the devices 12, 50, 51 and 52.

The scope of the invention is to be determined by the following claims rather than the foregoing description of preferred embodiments.

What is claimed is:

1. For use with a dental unit including a plurality of devices through which water can be passed from a pressurized water source through a primary water line into which one of pressurized air and disinfectant solution from respective sources thereof can be selectively introduced through a double inlet single outlet first router valve, a selectively operable removable purge unit for flushing and disinfecting said primary water line and devices comprising:

a) a solution reservoir for containing a disinfectant solution and ullage, b) a double inlet single outlet second router valve, c) an inlet air line removably connectable between the pressurized air source and alternately one of the reservoir ullage and a first inlet of the second router valve, d) a solution line between the solution reservoir and a second inlet of the second router valve, and e) a connection line for one of air and solution from the single outlet of the second router valve removably connectable to the primary water line, f) whereby water can be expelled from said primary water line and devices by pressurized air and replaced with disinfectant solution displaced by pressurized air from the ullage of the reservoir which solution can then be expelled by pressurized air and replaced with water.

2. A purge unit according to claim 1 wherein a pressure regulator is included in said air inlet line upstream of the reservoir ullage and the first inlet of the second router valve for reducing air inlet line pressure.

3. A purge unit according to claim 1 wherein first disconnect means are located in said inlet air line for removable connection with the pressurized air source, and second disconnect means are located in said connection line for removable connection with said primary water line.

4. In combination with a dental unit including a plurality of devices through which water can be passed from a pressurized water source comprising one of a water bottle and a water main through a primary water line into which one of pressurized air and disinfectant solution from respective sources thereof can be selectively introduced through a double inlet single outlet first router valve, a selectively operable removable purge unit for flushing and disinfecting said primary water line and devices comprising:

a) a solution reservoir for containing a disinfectant solution and ullage, b) a double inlet single outlet second router valve, c) an inlet air line removably connected by first disconnect means between the pressurized air source and alternately one of the reservoir ullage and a first inlet of the second route router valve, d) a solution line between the solution reservoir and a second inlet of the second router valve, and e) a connection line for one of air and solution from the single outlet of the second router valve removably connected by second disconnect means to the primary water line, f) whereby water can be expelled from said primary water line and devices by pressurized air and replaced with disinfectant solution displaced by pressurized air from the ullage of the reservoir which solution can then be expelled by pressurized air and replaced with water.

* * * * *